United States Patent
Abdulwaheed

(10) Patent No.: US 9,478,043 B2
(45) Date of Patent: Oct. 25, 2016

(54) MEASURING TEETH WHITENESS SYSTEM AND METHOD

(71) Applicant: Abdullaibrahim Abdulwaheed, Quincy, MA (US)

(72) Inventor: Abdullaibrahim Abdulwaheed, Quincy, MA (US)

(*) Notice: Subject to any disclaimer, the term of this patent is extended or adjusted under 35 U.S.C. 154(b) by 64 days.

(21) Appl. No.: 14/607,652

(22) Filed: Jan. 28, 2015

(65) Prior Publication Data
US 2015/0213622 A1    Jul. 30, 2015

Related U.S. Application Data

(60) Provisional application No. 61/933,112, filed on Jan. 29, 2014.

(51) Int. Cl.
| | |
|---|---|
| *G06K 9/00* | (2006.01) |
| *G06T 7/40* | (2006.01) |
| *G06T 7/00* | (2006.01) |
| *A61C 19/06* | (2006.01) |
| *A61C 13/08* | (2006.01) |
| *A61C 19/10* | (2006.01) |

(52) U.S. Cl.
CPC ........... *G06T 7/408* (2013.01); *A61C 19/066* (2013.01); *G06T 7/0012* (2013.01); *A61C 13/082* (2013.01); *A61C 19/10* (2013.01); *G06T 2207/30036* (2013.01)

(58) Field of Classification Search
CPC ............ G06T 7/408; G06T 7/0012; G06T 2207/30036; A61C 19/066; A61C 13/082; A61C 19/10
USPC .......................................................... 382/100
See application file for complete search history.

(56) References Cited

U.S. PATENT DOCUMENTS

| | | | | |
|---|---|---|---|---|
| 5,798,839 A * | 8/1998 | Berner | .................. | A61C 19/10 356/402 |
| 6,038,024 A * | 3/2000 | Berner | ..................... | G01J 3/02 356/326 |
| 6,190,170 B1 * | 2/2001 | Morris | .................. | A61C 19/10 433/203.1 |
| 6,358,047 B2 * | 3/2002 | Lehmann | ............... | A61C 19/10 356/408 |
| 7,064,830 B2 * | 6/2006 | Giorgianni | .............. | G01J 3/508 356/402 |
| 7,312,874 B2 * | 12/2007 | Berner | ...................... | G01J 3/10 356/402 |
| 7,463,757 B2 * | 12/2008 | Luo | .......................... | G01J 3/50 382/128 |
| 2002/0048400 A1 * | 4/2002 | Leedham | .................. | G01J 3/46 382/167 |
| 2006/0152586 A1 * | 7/2006 | Komiya | ............... | A61B 5/0088 348/207.99 |
| 2007/0255589 A1 * | 11/2007 | Rodriguez | .......... | G06F 19/3437 705/2 |
| 2008/0253651 A1 * | 10/2008 | Sagawa | .............. | G06K 9/00255 382/167 |
| 2008/0270175 A1 * | 10/2008 | Rodriguez | ............ | G06F 19/345 705/2 |
| 2008/0310712 A1 * | 12/2008 | Edgar | ...................... | H04N 1/62 382/167 |
| 2009/0181339 A1 * | 7/2009 | Liang | ................... | A61B 1/0638 433/29 |
| 2010/0284616 A1 * | 11/2010 | Dalton | ............... | G06K 9/00281 382/167 |
| 2012/0156634 A1 * | 6/2012 | Duff, Jr. | ................ | A61B 1/0016 433/29 |
| 2013/0129642 A1 * | 5/2013 | Joiner | .................... | A61K 8/345 424/54 |
| 2014/0146142 A1 * | 5/2014 | Duret | ................. | H04N 13/0242 348/47 |
| 2014/0330577 A1 * | 11/2014 | Herman | .............. | G06F 19/3418 705/2 |

* cited by examiner

*Primary Examiner* — John Strege
(74) *Attorney, Agent, or Firm* — Beck Tysver Evans, PLLC

(57) ABSTRACT

A method and system are presented for measuring the whiteness of teeth. This is accomplished by analyzing an average pixel value of teeth taken from a digital image. The pixel value is mathematically standardized to create an indicator that quantifies teeth whiteness. This eliminates subjectivity in measuring teeth whiteness and permits precise communication of the level of teeth whiteness.

14 Claims, 4 Drawing Sheets

MEASURING TEETH WHITENESS SYSTEM AND METHOD

CROSS REFERENCE TO RELATED APPLICATION

This application claims the benefit of U.S. Provisional Patent Application Ser. No. 61/933,112, filed on 28 Jan. 2014.

BACKGROUND OF THE INVENTION

The present invention relates to a method of measuring teeth whiteness and, more particularly, to a method of generating a single numerical teeth whiteness value using a mobile device.

The current systems for measuring the whiteness of teeth are confusing and subjective. All existing systems, including the most pervasive Vita guide, do not cover all colors of the visible electromagnetic spectrum. As can be seen, there is a need for a standardized method of measuring teeth whiteness.

SUMMARY OF THE INVENTION

A system and method are presented that allow a user to easily develop a "whiteness" score for their teeth. Traditional systems overemphasized color variations, needlessly complicating what most users want to know—"how white are my teeth, and are they getting whiter?" One embodiment of the present invention allows a user to use a camera on a mobile device to take a photograph of their teeth. The user examines the photograph and selects a point on a tooth. The system examines the color value (such as R-G-B color values) of pixels surrounding that point, rejects pixels that vary greatly from the typical value, develops an average color value for the remaining pixels, and applies an algorithm to develop a 1-100 score based on this color value. The mobile device can share this score with a centralized server. The server can compare this value with other users, and return a normalized percentile score compared to other users. Historical values for a user can be compared with the most recent value to determine any improvement in a user's whiteness score.

Because the R-G-B value of pixels in an image depend heavily on the color and intensity of the light and the exposure of the image, it can be difficult to compare the whiteness value of teeth in one image with the whiteness of teeth in a different image taken in different lighting conditions or different exposure values. One embodiment overcomes this difficulty by including reference item within the image. For instance a standard gray card or other reference paper or device can be included in the same image as the user's teeth. Such a device can be used to normalize both the exposure and white balance of an image, ensuring that the overall lighting and color balance of images will be consistent with one another. In other embodiments, the reference item would include a plurality of shaded areas, each have a different whiteness value that is typical for most teeth. In this embodiment, the mobile device can compare the whiteness calculated for a user's teeth against this comparison chart to find the closest match.

BRIEF DESCRIPTION OF THE SEVERAL VIEWS OF THE DRAWING(S)

DETAILED DESCRIPTION OF THE INVENTION

Figure 1:
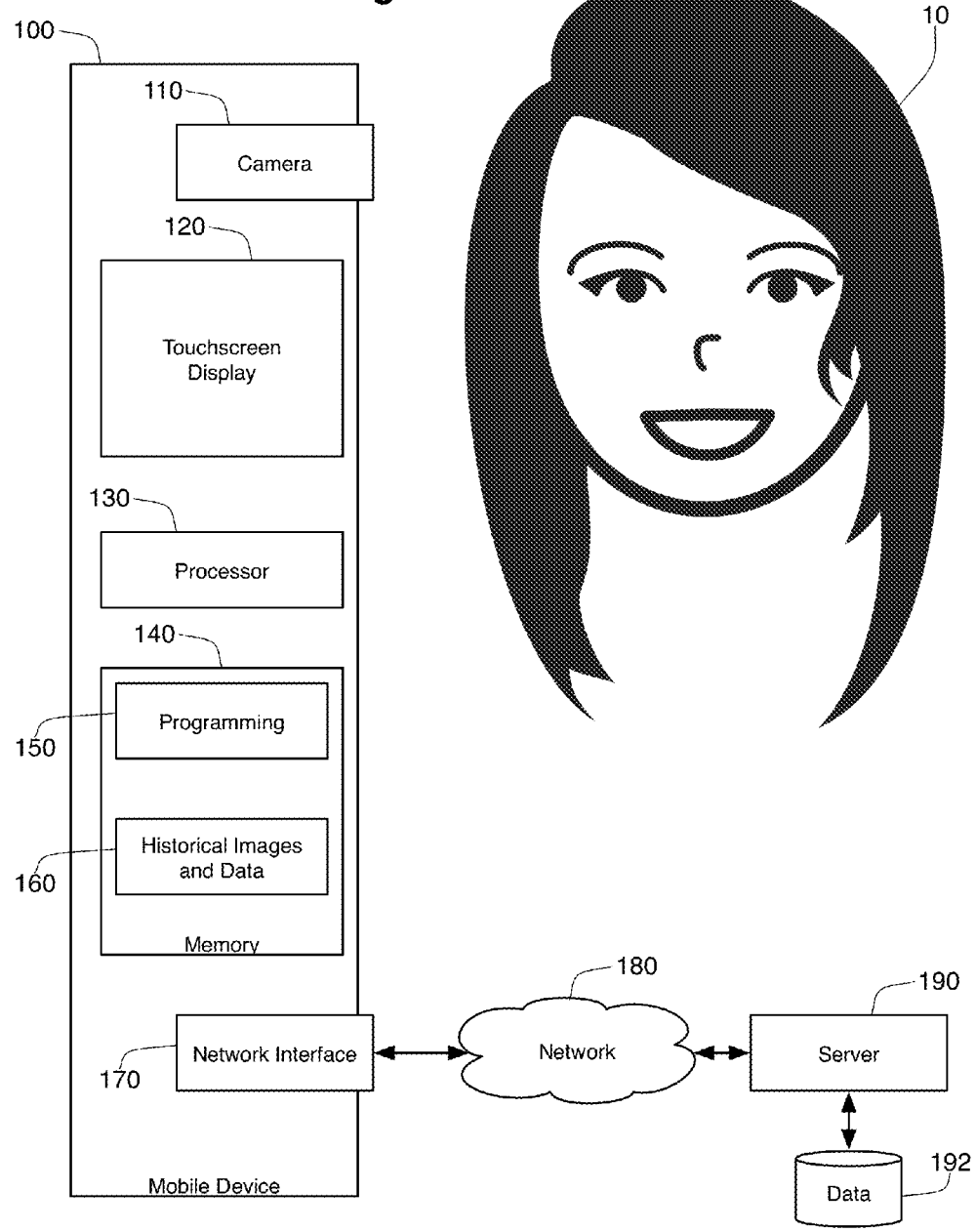
FIG. 1 is an schematic view of a mobile device and its internal components as it takes an image of a person's teeth.

In FIG. 1, a mobile device 100 is shown that can take images of a user 10 in order to establish a value for the whiteness of the user's teeth. The mobile device 100 takes the image through an integrated camera 110. The user can use a touchscreen display 120 to aim the camera 120 and to record the image. In the preferred embodiment, touch screen 120 both presents visual information to the user over the display portion of the touch screen 120 and also receives touch input from the user. The recording of an image using the camera 110 and display 120 is allowed through use of a mobile device processor 130, which operates under the guidance of programming instructions 150 that are stored on non-volatile memory 140 of the device 100. The instructions 150 can instruct the processor 130 on how to record an image, and also on how to calculate a whiteness value for teeth found in the image.

In FIG. 1, the mobile device 100 uses a network interface 170 to communicate over network 180 with a remote server 190. The remote server can store and recall data from a database 192, which may be locally connected to the server 190 or can be accessed by the server 190 over a network. In one embodiment, the network 180 is a wide area network such as the Internet. In one embodiment, the data network interface 170 connects the device 100 to a local wireless network that provides connection to the wide area data network 180. The network interface 170 preferably connects via one of the Institute of Electrical and Electronics Engineers' (IEEE) 802.11 standards. In one embodiment, the local network is based on TCP/IP, and the data network interface 170 utilizes a TCP/IP protocol stack. In other embodiments, the network 180 is formed in part by a cellular data network. In these embodiments, the network interface 170 takes the form of a cellular communication interface that communicates over the cellular network 170.

In other embodiments, the programming that operates the method described below is stored remotely and is accessed over the network 180. For instance, a web browser could operate on the mobile device 100 using locally stored programming 150, and could access a website or other remote programming over network 180. This remote programming could provide the interface for creating an image, determining a whiteness value for a user's teeth, and storing and comparing this values to other values stored on the remote server 190.

The mobile device 100 can take the form of a smart phone or tablet computer. The mobile device processor 130 can be a general purpose CPU, such as those provided by Intel Corporation (Mountain View, Calif.) or Advanced Micro Devices, Inc. (Sunnyvale, Calif.), or a mobile specific processor, such as those designed by ARM Holdings (Cambridge, UK). Mobile devices such as device 100 generally use specific operating systems 140 designed for such devices, such as iOS from Apple Inc. (Cupertino, Calif.) or ANDROID OS from Google Inc. (Menlo Park, Calif.). The operating system programming 150 is stored on memory 140 and is used by the processor 130 to provide a user interface for the touch screen display 120, handle communications for the device 100, and to manage and provide services to applications programming (or apps) 150 that are stored in the memory 140.

In other embodiments, the image is taken with a laptop or desktop computer (not shown in FIG. 1). Such computing devices frequently have integrated cameras, but may also include external cameras connected to the computer through an expansion bus, such as a USB connection. These computers can then perform the method described below in connection with FIG. 3. For ease in describing the present invention, the description below will refer to the use of a mobile device to acquire an image, determine a whiteness value for the user's teeth, and to communicate with the server 190.

Figure 2:
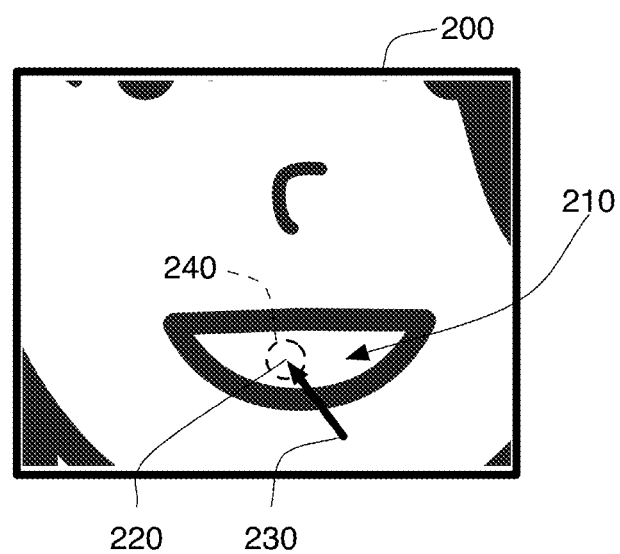
FIG. 2 is schematic representation of a touchscreen display showing an image taken by the mobile device and the elements necessary to select a location for analysis.

FIG. 2 shows an image 200 of the user 10 taken with camera 110. This image 200 is displayed by the mobile device 100 on the touchscreen display 120 after the image is acquired. The present invention uses an image such as this to determine a whiteness value for the user's teeth 210.

Figure 3:
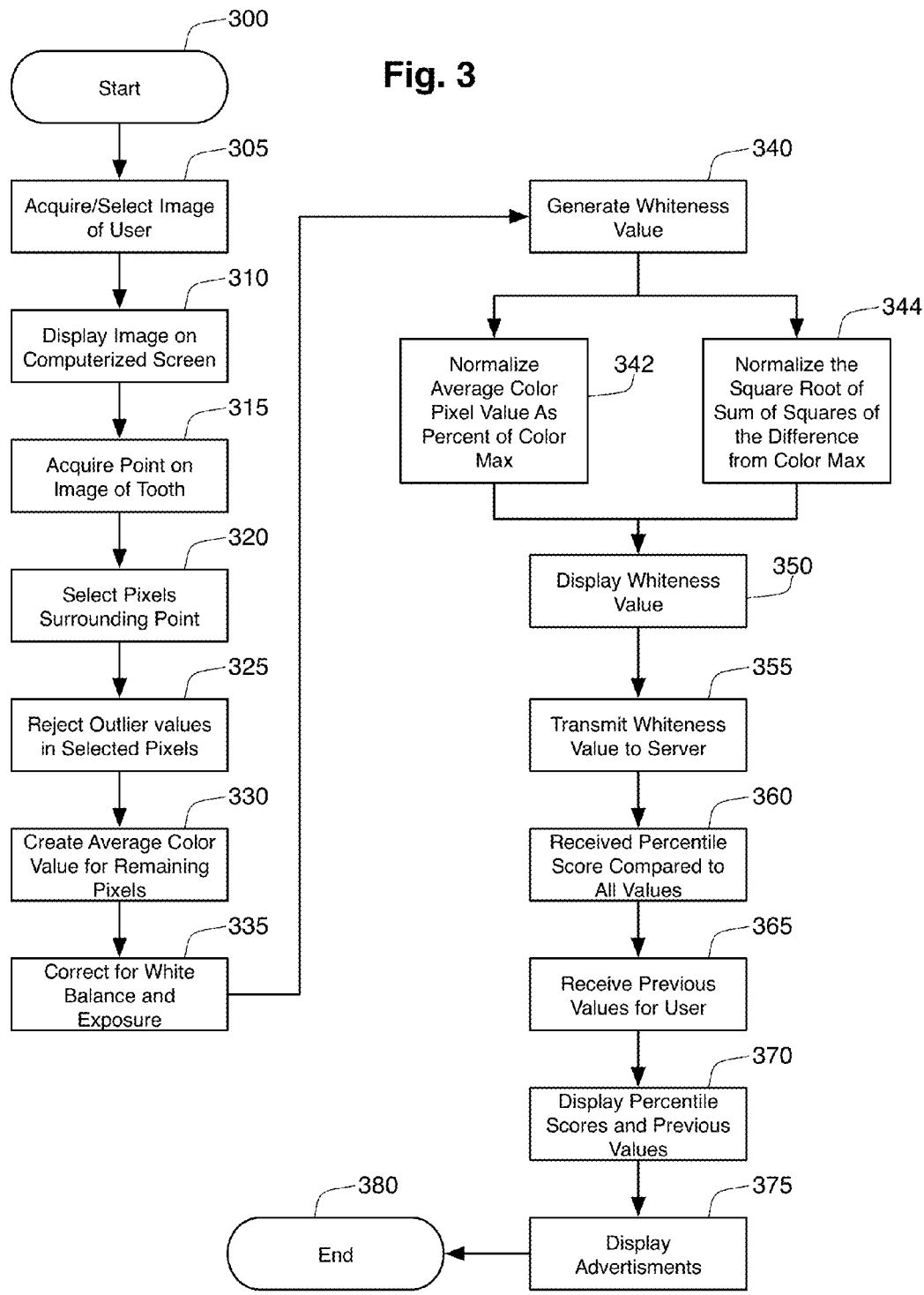
FIG. 3 is flow chart showing a method that can be use to implement an embodiment of the present invention.

A method 300 for determining the whiteness value using this image 200 is shown in the flow chart of FIG. 3. The method 300 begins at step 305 by having the programming 150 direct the user 10 to acquire an image 200 of their teeth 210. This image 200 can be created using the camera 110 built into the mobile device 100. Alternatively, the user can select a previously recorded image that is stored either in the memory 140 of the device 100 or selected and retrieved from a remote photographic storage location over the network 180 and the network interface 170. At step 310, the image 200 is shown in the touchscreen display 120 of the mobile device. The user is then asked to select a location or point 220 on the image that corresponds to one or more of the user's teeth 210. In FIG. 2, the user 10 manipulates a pointing device 230 on the display 120 until the pointing device is pointed at the teeth 210 in the image 200. In other embodiments, the user simply presses on the touchscreen display at this location 220. In still other embodiments, the device 100 uses programming to analyze the context of the image (such as through the use of facial recognition software) and to automatically identify the teeth of the user in the image 200.

At step 320, the method 300 selects a group of pixels 240 surrounding this location 220 (step 320). In one embodiment, the programming 150 automatically selects a group of pixels 240 surrounding the selected point. For example, the programming 150 could select a circular region having a radius of approximately 10 pixels centered on the selected point 220. Other shaped and sized regions could also be automatically selected, such as a 10×10 pixel square area centered on the point 220, or a circle with a radio of 5 or 20 pixels. In still other embodiments, the user is allowed to select a group of pixels 240 instead of only a single point 220 on the image, such as by dragging their finger across an area of the image 200 presented in the touchscreen display 120. In still further embodiments, the user is allowed to select non-contiguous pixels on the image 200 as part of step 320, such as by individually selecting the center of each tooth displayed in the image 200. Note that in some cases, the selected pixels may be from a single tooth in the image 200 and in other cases the pixels may be from multiple teeth. For purposes of this disclosure, pixels relating to a user's "teeth" should be understood to relate to both situations unless otherwise specified.

In step 325, statistical analysis is used to reject pixels within the selected group of pixels 240 that represent outlier values. There are numerous statistical techniques that can be used in this analysis, such as Dixon's Q test. To perform this test, the value of each pixel will need to be compared with the value of the other pixels in the group 240. In most color images, pixels are represented by three or four separate values. For instance, in RGB representations, each pixel has a red (R) value, a green (G) value, and a blue (B) value. Other color schemes are also possible, such as CMY (having values for cyan, magenta, yellow), CMYK (similar to the CMY color scheme with an added key or black color), HSL (having values for hue, saturation, and lightness), or HSV (hue, saturation, and value). The test for outliers can be performed on each of these separate elements (R, G, and B values, for instance, in an RGB color representation scheme). Alternatively, this test can be performed on a universal number derived from these separate elements, such as the whiteness value described below in connection with steps 340-344. Either way, this analysis removes pixels that may not accurately reflect the whiteness value of the user's teeth 210. For instance, the rejected pixels may actually be part of the user's lips or gums, or may represent a shadow area inside the user's mouth.

Once outlier pixels are removed from the selected pixels 240, the remaining pixels are averaged to create values for an average pixel. In most cases, the individual elements of a pixel (such as the R, G, B values) are averaged across all of the remaining pixels to create a single (R,G,B) value for the pixel set 240. This occurs at step 330.

Unfortunately, this average pixel value may not be an accurate representation of the brightness or color of a user's actual teeth 210. This is because the pixel value of the teeth in the image 210 is heavily dependent on the lighting that existed on the user's face when the image was taken, and on the exposure of the image taken by the camera 110. If the camera 110 is designed to automatically expose the image 200, the exposure of the user's teeth will depend on the average brightness of the rest of the image 200, as the camera 110 will try to balance the exposure of the overall image 200. In other words, a dark background may overexpose a user's teeth, creating higher values relating to the brightness or individual color values of the average pixel determined at step 330. In addition, as different lighting sources have different colors, these different light sources may change the overall color or white balance of the image. In one embodiment, this limitation of the pixel values in the image 200 is overcome by requesting that the user take the image 200 under a standard lighting condition. The actual lighting recommended makes little difference, as long as the lighting conditions remain relatively constant from image to image. For a single user, they can track whiteness changes in their teeth over time in an accurate manor by simply repeating the images 200 under the same lighting conditions using the same exposure settings on their camera 110. Even when users repeat their lighting conditions over multiple images, it is still difficult to compare the whiteness of teeth calculated for one user with the whiteness calculated for a different user, as the different users will likely be unable to create identical lighting conditions. One can give instructions to all users on how to take the image, but each user will likely interpret the instructions differently.

Figure 4:
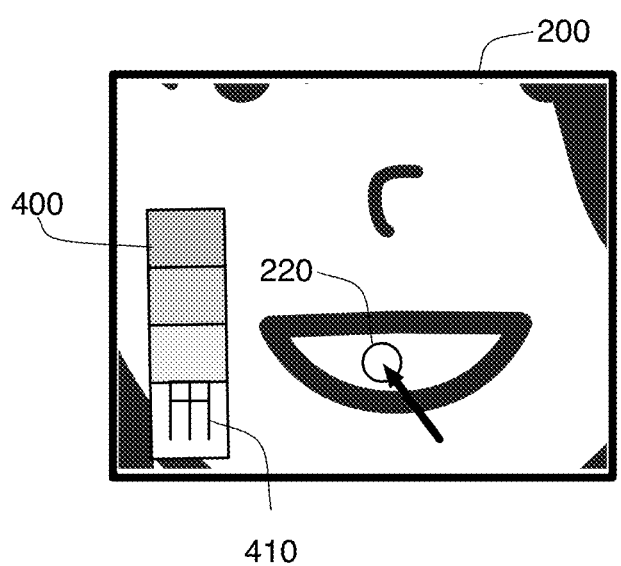
FIG. 4 is a schematic representation of the touchscreen display of FIG. 2 with the addition of a reference device within the image.

To overcome this limitation, one embodiment of the present invention has the user take their image 200 with a reference card 400 also visible in the image, as seen in FIG. 4. This reference card may be a standard "gray card," such as a neutral gray card having 18% reflectivity across the visible spectrum. In order to make the card 400 easy for the programming 150 to automatically detect in the image, the reference card 400 may contain a pattern of blocks or an icon 410 that can be detected through digital analysis of the image 200. In FIG. 4, the card contains both a pattern of blocks, going from white to darker gray as one moves up the card 400 in the image 200, and a computer recognizable icon 410. The programming scans the image 200 for the presence of the card 400. If identified, a location on the card having a pure gray color of a known reflectivity is identified. Pixels on this card location are then analyzed in order to standardize both the exposure of the image 200 and the white balance of the image 200. This standardization is then applied to the average value selected in step 330, in order to create a corrected pixel value in step 335.

At step 340, a whiteness value is created for this corrected pixel value. In the preferred embodiment, a single number is create for this whiteness value in order to inform the user how "white" their teeth are. Multiple algorithms can be applied to the corrected pixel value in order to create this whiteness value. FIG. 3 shows two different options.

The first option 342 examines the individual color values of the pixel. This works best in an RGB or CMY type of color schema, where brightness or blackness of the pixel is not a separate value. The RGB color scheme is ideal for describing the present invention, as higher numbers in this color scheme equal brighter values, and where maximum values for each color results in a pure white color for a pixel. In this type of environment, one can simply take an average of the three colors, and then normalize this number against a maximum value. When the RGB values are recorded as 8-bits each, each of the three colors for a pixel has a range from 0-255. The normalized average would be the sum of the three color values divided by three (to create the average), with the total divided by 255 (creating a number from 0-1). This number can again be multiplied by 100 to create a value from 1-100. The algorithm can be expressed as:

$$((R+G+B)/3)/255)*100$$

In a 16 bit environment, each RGB color value can range from 0 to 65,536, resulting in the following algorithm to create the same normalized average result:

$$((R+G+B)/3)/65,536)*100$$

In a CMY color scheme, the pixel can be converted to RGB with the above algorithm applied. Alternatively, with the assumption that C=Max−R, M=Max−G, and Y=Max−B, the 8-bit algorithm for CMY colors would be:

$$(((255-C)+(255-M)+(255-Y))/3)/255)*100$$

The conversion of the 16-bit RGB algorithm to CMY would be done in the same manor.

One issue with the average value created by option 342 is that discolored teeth are given the same score as pure white/grey teeth of the same overall brightness or intensity. A second option (step 344) corrects this problem by lowering scores for teeth whose color is not pure white/grey. In this option, the difference of each color value from the maximum value (such as 255−R for the red color in an 8-bit RGB color scheme) is squared. The squared value for each color are then summed together, and the square root of this value is then taken. This number is then normalized compared to the maximum possible value. In an 8-bit RGB color scheme, pure black is 0,0,0, and pure white is 255,255,255. To create a whiteness value where pure black is still 0, and pure white is 100, and discolored teeth have a lower value that pure white/grey teeth of the same brightness, the following formula can be applied:

$$((441.673-((R-255)^2+(G-255)^2+(B-255)^2)^0.5)/441.673)*100$$

In this formula, the difference of each value from the maximum (255) is determined and squared. These numbers are added together, and the square root is taken. The range of this value from pure black to pure white is from 441.673 (pure black) to 0 (pure white). This number is subtracted from 441.673 (now pure white is 441.763 and pure black is 0), and the resulting value is divided by 441.673 and multiplied by 100 to get a range from 0 (pure black) to 100 (pure white).

In a 16-bit RGB environment, the formula is the same with the constants changing to represent the new maximum values. The maximum score ("MaxScore") for the square root of the sum of the squares can be determine by the following formula based on the maximum value ("MaxValue") for each color of a pixel (65,536 colors in a 16-bit environment)

$$MaxScore=((MaxValue^2)*3)^0.5$$

In a 16-bit environment, the MaxValue is 65,536, meaning that the MaxScore is approximately 113,511.682. Note that the MaxScore in this calculation need not be exact, as this formula will typically result in a number that is not accurately represented in only a few digits. Thus, the MaxScore can be approximated, such as by using a MaxScore value of 440 in an 8-bit RGB environment, or a MaxScore value of 113,000 in a 16-bit RGB environment. Generally, using a MaxScore value having at least two significant digits in common with the calculation above is sufficient.

If we use the MaxScore and MaxValue variable names, the resulting normalization formula for an RGB color scheme is:

$$((MaxScore-((R-MaxValue)^2+(G-MaxValue)^2+(B-MaxValue)^2)^0.5)/MaxScore)*100$$

The conversion of the general formula to CMY would be clear to one of ordinary skill in the art. Note that this formula can be implemented with several variations while still keeping within the scope of the present invention. For instance, the formula may equate a pixel color value of less than the maximum value to be a maximum value for the purposes of the formula. Thus, the maximum value for any color in an 8-bit RGB color scheme may be set at less than the theoretical maximum value (such as 250 or above). Thus an 8-bit RGB value of (251, 254, 253) would be reduced to the maximum score of (250, 250, 250), and be given a whiteness score of 100.

By applying one of these formulas 342, 344, method 300 standardizes and quantifies the level of whiteness for teeth. This provides a defined metric for a near infinite spectrum of teeth whiteness, which allows the consumer to measure the whiteness of their teeth against pure white. At step 350, this value is displayed to the user, such as on display 120, giving the user an understandable answer to the question as to the whiteness of their teeth.

In another embodiment, the reference card 400 can include a plurality of different shaded areas. Each of these shaded areas will have a different whiteness value. Preferably, these different areas would have whiteness values that extended through a range of whiteness that is common in human teeth. The processor 130 can then compare the selected area 240 of the user's teeth with the various shaded areas on the reference card. Because the processor 130 would be aware of the whiteness score for each of these different shaded areas, a whiteness match between the teeth and a particular area on the reference card would establish a definitive whiteness score for the user's teeth. This can be accomplished without the need to correct for exposure and white balance, as the reference card has received the same exposure and lighting as the user's teeth. If the teeth had a whiteness level that fell between two areas on the reference card, the whiteness score for the teeth would be known to be between the two pre-established whiteness values for those areas of the card. This whiteness comparison can be accomplished by calculating the whiteness value for both the teeth and the various areas on the card using the calculations described above.

In step 355, the mobile device transmits this calculated value, along with a user identifier, to the remote server 190. The server 192 will store this data in its database 192, allowing the user to compare this value to similar values previously calculated for their teeth, and against similar values calculated for other users. In one embodiment, the sever 190 compares the received value against all other values for all users in the database 192 in order to give the score a percentile rank. This rank is returned to and received by the mobile device 100 in step 360. The server 190 can also send all previous scores for this user back to the mobile device 100, which is received at step 365. In alternate embodiments, the mobile device 100 keeps historical data and images 160 from previous calculations in its local memory. In these embodiments, the mobile device 100 would not need to receive such historical information from the remote server 190 in step 365.

At step 370, the percentile ranking and the comparison to historical values are displayed to the user on the display 120 of the mobile device. The user can then examine this data, and even request to see historical pictures of themselves. In this manner, the user can track their progression as they attempt to whiten their teeth.

In some instances, the mobile device 100 may present advertisements to the user as they perform method 300. This is shown in FIG. 3 as step 375, although the advertisements may be displayed at any step in the method 300. Preferably, these advertisements relate to products and services that allow the user 10 to brighten her teeth. These advertisements can be transmitted when needed from the server 190, or can be stored locally in the mobile device 100.

In other embodiments, the user is able to use the mobile device to track cosmetic treatments to their teeth. The mobile device can then compare and contrast numerically the whiteness of the user's teeth before and after these cosmetic treatments.

While the invention has been described with reference to an exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments described herein, but that the invention will include all embodiments falling with the scope of the appended claims.

I claim:

1. A computerized method for determining a whiteness score for a user's teeth comprising:
   a) at a computing device, identifying a plurality of pixels from an image that show a portion of the user's teeth;
   b) at the computing device, determining an average pixel value for the plurality of pixels;
   c) at the computing device, determining a plurality of color values for the average pixel;
   d) at the computing device, evaluating the plurality of color values to generate the whiteness score for the average pixel, wherein the whiteness score is a single numerical value calculated based on analysis of a red color value (R), a green color value (G), and a blue color value (B) for the average pixel, further wherein the whiteness score is based on taking a square root of a sum, the sum being the total of the square of (the R value minus a maximum R value), the square of (the G value minus a maximum G value), and the square of (the B value minus a maximum B value); and
   e) at the computing device, displaying the whiteness score.

2. The computerized method of claim 1, wherein the whiteness score is normalized to a scale from 0 to 100.

3. The computerized method of claim 2, wherein the whiteness score is approximated using the formula:

$$((\text{Max-Score} - ((R - \text{MaxValue})^2 + (G - \text{MaxValue})^2 + (B - \text{MaxValue})^2)^{0.5}) / \text{MaxScore}) * 100$$

wherein the MaxValue is a maximum value for a color value, and wherein the MaxScore is approximately equal to the square root of three times the MaxValue squared.

4. The computerized method of claim 3, wherein the R, G, and B values are represented by eight bits, the MaxValue is 255, and the MaxScore is approximately 440.

5. A computerized method for determining a whiteness score for a user's teeth comprising:
   a) at a computing device, identifying a plurality of pixels from an image that show a portion of the user's teeth;
   b) at the computing device, determining an average pixel value for the plurality of pixels;
   c) at the computing device, determining a plurality of color values for the average pixel;
   d) at the computing device, evaluating the plurality of color values to generate the whiteness score for the average pixel, wherein the whiteness score is a single numerical value calculated based on analysis of three different color values for the average pixel, further wherein the whiteness score is based on taking a square root of a sum, the sum being the total of the square of (a first color value minus the maximum possible value), the square of (a second color value minus the maximum possible value), and the square of (a third color value minus the maximum possible value); and
   e) at the computing device, displaying the whiteness score.

6. The computerized method of claim 5, wherein the step of identifying the plurality of pixels from the image further comprises determining a point in the image where the user's teeth are shown.

7. The computerized method of claim 6, wherein the step of identifying the plurality of pixels from the image further comprises selecting pixels surrounding the point.

8. The computerized method of claim 7, wherein the step of identifying the plurality of pixels from the image further comprises using statistical analysis to remove outlier pixels from the plurality of pixels.

9. The computerized method of claim 5, wherein the computing device is a mobile device selected from a set comprising a tablet computer and a smart phone.

10. The computerized method of claim 9, further comprising acquiring the image from a camera integrated into the mobile device.

11. The method of claim 5, further comprising:
   f) at the computing device, displaying historical data of at least one prior whiteness score for the user.

12. The method of claim 5, further comprising:
- f) at the computing device, transmitting the whiteness score to a remote server over a wide area network using a network interface on the computing device;
- g) at the computing device, receiving a percentile score from the remote server indicating a percentile ranking of the whiteness score relative to other whiteness scores received by the remote server from other computing device; and
- h) at the computing device, displaying the percentile ranking.

13. The method of claim 5, further comprising:
- f) at the computing device, displaying an advertisement relating to teeth whitening when displaying the whiteness score.

14. The method of claim 5, wherein the step of determining the average pixel value further comprises:
- i) identifying a reference object in the image,
- ii) using the reference object to standardize the exposure and white balance of the image, and
- iii) determine the average pixel value after standardizing the exposure and white balance of the image.

\* \* \* \* \*